United States Patent [19]

Mazzetti

[11] 4,044,617
[45] Aug. 30, 1977

[54] MULTI-STAGE SAMPLER FOR FLOWING MATERIAL

[76] Inventor: Flavio J. Mazzetti, 6580 Arequa Ridge Lane, Colorado Springs, Colo. 80919

[21] Appl. No.: 726,808

[22] Filed: Sept. 27, 1976

[51] Int. Cl.² .............................................. G01N 1/14
[52] U.S. Cl. ........................................................ 73/424
[58] Field of Search .............................. 73/421 A, 424

[56] References Cited

U.S. PATENT DOCUMENTS

| | | | |
|---|---|---|---|
| 649,288 | 5/1900 | Fanders | 73/424 |
| 3,250,131 | 5/1966 | Jordison | 73/424 |

*Primary Examiner*—S. Clement Swisher
*Attorney, Agent, or Firm*—Richard W. Hanes

[57] ABSTRACT

A multi-stage sampler for providing a representative sample of a batch of flowing material such as wet or dry sand, mineral concentrates, grain, sicky material, particulate matter, and the like. The sample includes a rotating sampler disc onto which the batch is delivered. This sampler disc has holes in it near its perimeter. A stationary guide means is positioned above the rotating disc to direct the material radially outward over the holes and into a discharge chute. A sample of the batch falls through the holes and is received within a second stationary guide means located above an annular, rotating conveyor disc. The sample is conveyed across the conveyor disc along a predetermined path defined by its guide means. The guide means has a deflecting member that deflects the sample off the annular conveyor disc through its central hole. A second sampler disc substantially identical to the first one receives the sample and, in a manner substantially identical to the first sampling disc, samples the sample. This procedure is repeated until a small, representative sample is produced. All of the discs rotate about the same vertical axis. The material passing through the sampler is being continuously tumbled and mixed to help create a truly representative sample. A reciprocating scraper is positioned above the top sampler disc to clean its surface between batches and an inclined chute is provided below each sampler disc to direct the flow discharging from the sampler disc into the discharge chute.

9 Claims, 9 Drawing Figures

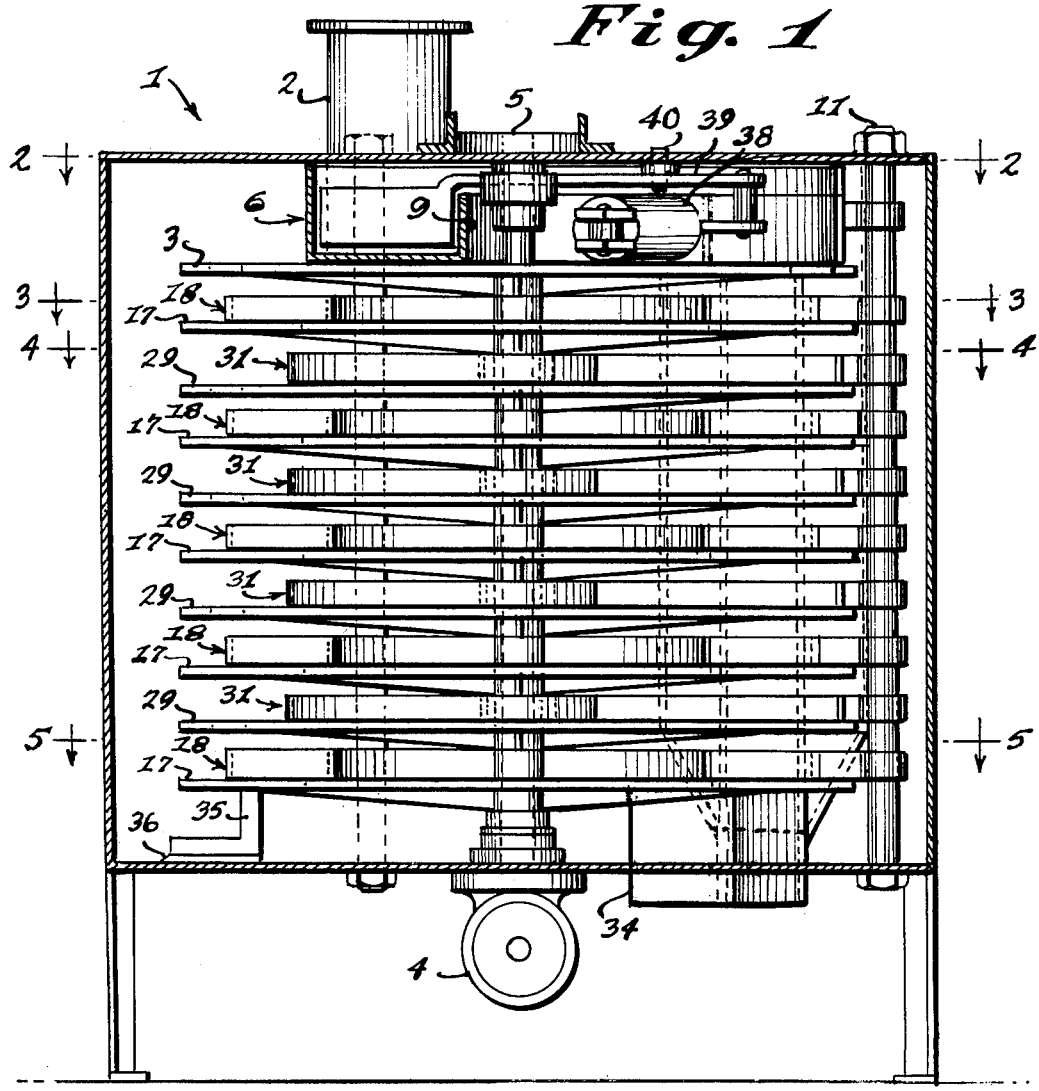
*Fig. 1*
*Fig. 6*
*Fig. 7*
*Fig. 9*

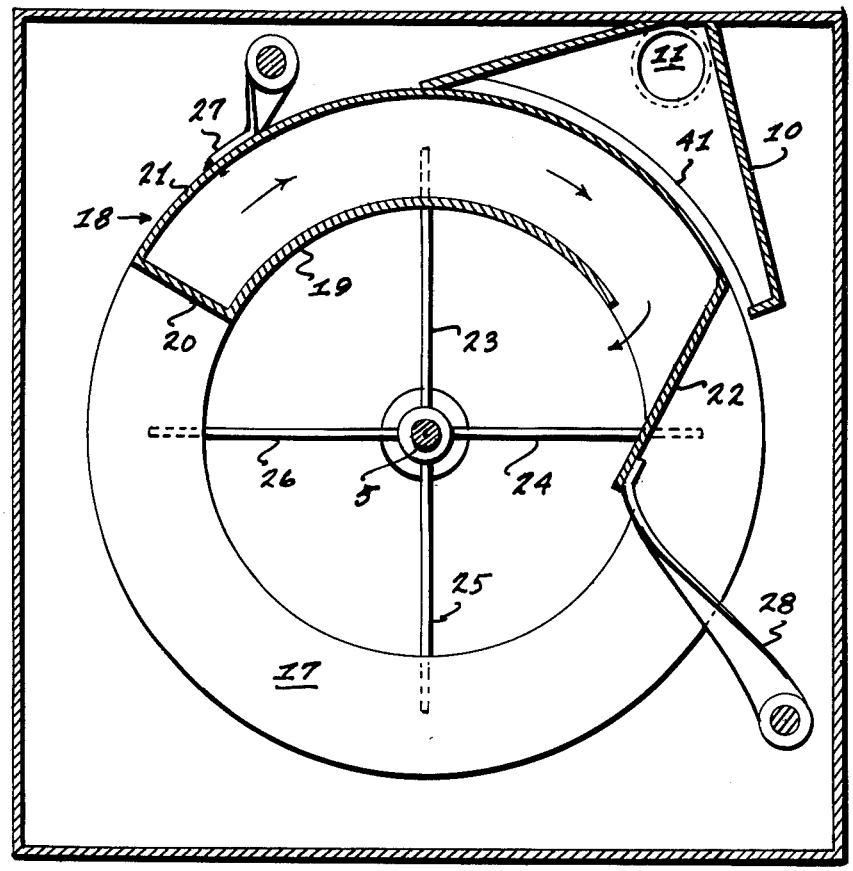
Fig. 3
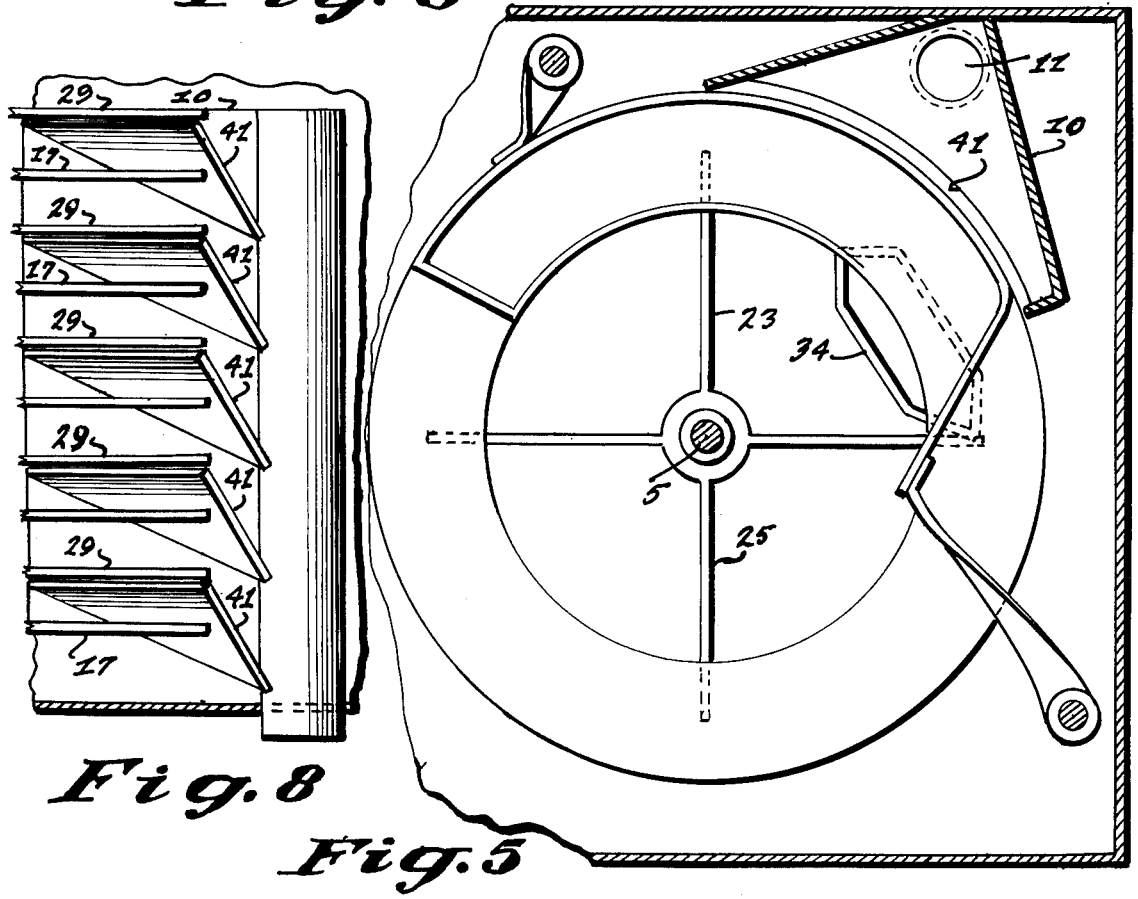
Fig. 8
Fig. 5

MULTI-STAGE SAMPLER FOR FLOWING MATERIAL

BACKGROUND OF THE INVENTION

The ideal flow sampler would capture every particle in the flow for testing. Since this is not practical, samplers that capture a large percentage of the flow are often used; however, these samplers result in a large volume of sample material that must be handled and tested. This method has also been found to be impractical. Multi-stage samples that, in essence, sample the sample are a very effective solution to this problem of producing a small but representative sample from a large, initial sampling.

PRIOR ART

In most multi-stage samplers, a relatively large initial sample is taken. Generally, the larger the sample, the more representative it is of the flow. The initial sample is then collected and mixed before it itself is sampled. This procedure can be repeated until a small but representative sample is produced.

U.S. Pat. No. 1,964,755 to Stuart is of this general type. Stuart's multi-stage sampler is for liquids. It has an upper tank with numerous evenly spaced holes in its bottom. All of the holes but one empty into a main, lower tank. The remaining hole empties into a small vessel. This process is then repeated in his second stage whereby the small vessel also has holes in its bottom. All but one of these holes empties into the main, lower tank. The remaining hole empties into yet a smaller vessel. In this manner, a sample of the initial sample is taken. Stuart's sampler has no moving parts and no mixing means. It would appear to work only with free-flowing liquids or solutions.

Multi-stage samplers of flowing particular material are often bulky and require a lot space. This bulk is often caused because the sampler has one apparatus to take the initial sample, a separate apparatus to receive the sample, another to mix it, another to sample the initial sample, and a final apparatus to return the excess to the main flow. Typically, a diverter deflects an initial sample from a belt conveyor into a receiving chute which empties through a mixer onto another belt conveyor where a second diverter deflects a sample of the initial sample. Often a separate belt conveyor is needed to return the excess back to the main flow.

U.S. Pat. No. 2,405,951 to Herrold shows a typical, bulky sampler. In Herrold's one-stage sampler, material is dropped through a series of stationary baffles which mix the material as it falls. A diverter in the path of the flow then deflects a sample of the falling material. A multi-stage sampler based on this stage would be very large and cumbersome.

OBJECTS OF THE INVENTION

It is an object of this invention to provide a multi-stage sampler that is compact.

It is also an object to provide a sampler that can take a representative sample of flowing material such as wet or dry sand, ores, grain, particulate material, sticky material, and the like.

It is a further object of this invention to provide a sampler whose basic sampling procedure can be repeated in successive stages until a representative sample of any desired size is produced.

BRIEF DESCRIPTION OF THE DRAWINGS

FIG. 1 is a cross-sectional side view of the invention.

FIG. 3 is a plan view taken along lines 3—3 of FIG. 1 showing the conveying stage of the invention.

FIG. 5 is a plan view along lines 5—5 of FIG. 1 showing the final conveying stage which discharges into the sample chute.

FIG. 6 is a cross section of a sampler disc.

FIG. 7 is a cross section of a conveyor disc.

FIG. 8 is a cross-sectional view showing the inclined chutes which are attached to the discharge chute and extend below and across the flow discharging from each sampler disc to direct the flow into the discharge chute.

FIG. 9 is a simplified flow diagram of the sampling technique used in the mutli-stage sampler to produce a small, representative sample. Each of the three stages shown has a sampler disc and a conveyor disc. In each stage, a sample of the material delivered onto the sampler disc is taken and delivered onto the next lower stage. The bulk of the material on each sampler disc is discharged radially outwardly to the main discharge flow. The final sample emerging from stage three is a small but representative sample of the batch of material initially delivered onto the sampler disc of the first stage.

DETAILED DESCRIPTION OF THE INVENTION

Figure 2:
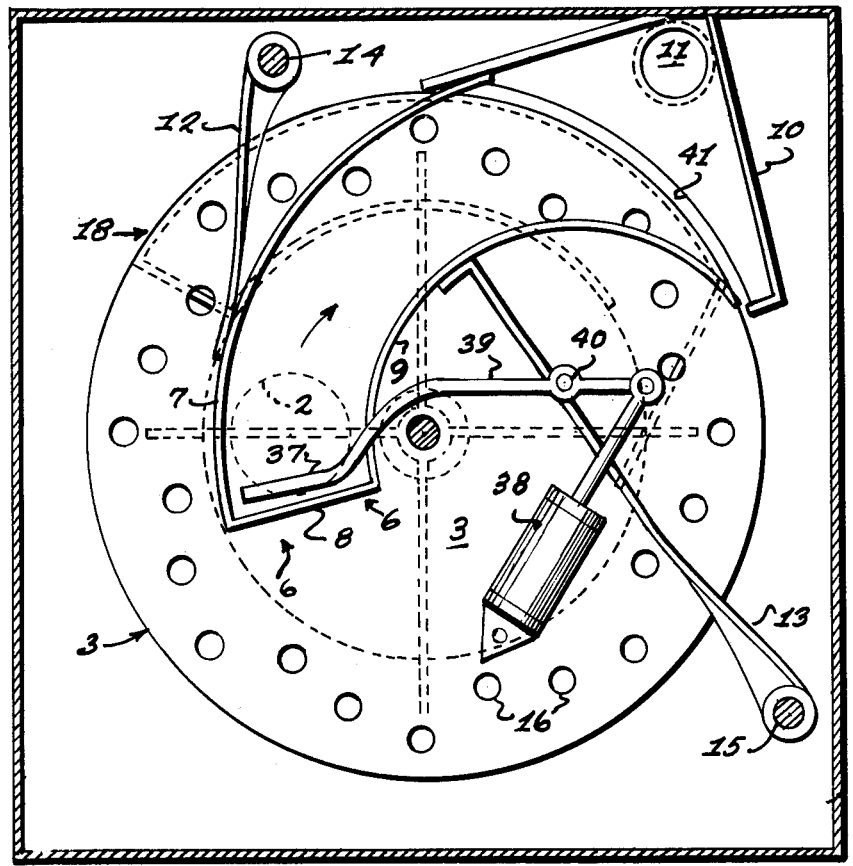
FIG. 2 is a plan view taken along lines 2—2 of FIG. 1 showing the initial sampling stage of the invention with its reciprocating scraper. The phantom lines show the guide means of the conveyor disc immediately below it.

As best seen in FIGS. 1 and 2, the multi-stage sampler 1 has an inlet member 2 through which the batch of material is fed onto a rotating sampler disc 3. The sampler disc 3 is rotated by motor 4 about a vertical axis defined by shaft 5. The entire batch of material is delivered onto the disc 3 within the bounds of stationary guide means 6 which is positioned just above the disc 3. As shown in FIG. 2, sides 7-9 of the guide means confine the flow across the disc 3 to a predetermined path from below the inlet member 2 to the discharge chute 10. Discharge chute 10 is supported by tube 11. Support arms 12 and 13 connected to shafts 14 and 15 hold the stationary guide means 6 in its position just above the disc 3. The guide means is preferably held in a touching relationship to the disc but can be slightly spaced therefrom as long as the spacing is smaller than the smallest particle in the flow.

The sampling disc 3 in FIG. 2 has an annular section near its circumference with holes 16 in it. When the disc is rotated, material is conveyed within the guide means 6 over the holes 16. A sample of the flow falls through the holes 16 onto the rotating conveyor disc 17 of FIG. 3.

As seen in FIG. 3, rotating conveyor disc 17 is annular defining a large hole in its center. It has a stationary guide means 18 with sides 19-22. As shown in the phantom lines of FIG. 2, the guide means 18 of the conveyor disc 17 is located underneath the annular section of disc 3 with the holes 16 in the region of the flow path across disc 3. All of the initial sample from disc 3 is received on conveyor disc 17 within its guide means 18. Disc 17 is attached by arms 23-26 to the shaft 5. Supporting arms 27 and 28 hold the stationary guide means 18 in its position above the disc 17. All of the sample falling on disc 17 is conveyed on the disc within its guide means 18 and is deflected by deflecting side 22 of the guide means into the hole defined by annular disc 17.

Figure 4:
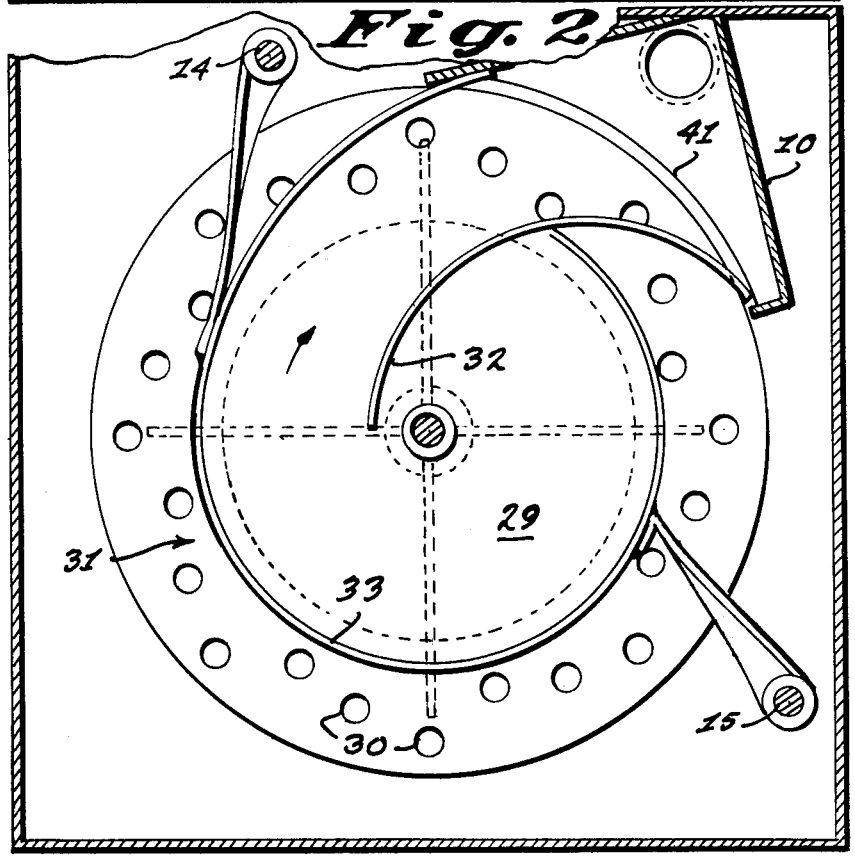
FIG. 4 is a plan view taken along lines 4—4 of FIG. 1 showing the basic sampling stage of the invention. This basic sampling stage is repeated in all the lower sampling stages. The only difference between the sampling stages of FIGS. 2 and 4 is the placement of the guide means.

Located below conveyor disc 17 is another rotating sampler disc 29 as shown in FIGS. 1 and 4. The sampler disc 29 with holes 30 is substantially identical to sampler disc 3, however, its stationary guide means 31 is slightly different. Comparing FIGS. 2 and 4, the sides 32 and 33 of guide means 31 meet to enclose a larger area than guide means 6. In the illustrated embodiment, the two guide means are different, however, they could be made identical without departing from the scope of the invention. In the illustrated embodiment, the guide means of every sampler disc but the first is substantially identical.

All of the initial sample falling from disc 17 is received within the guide means 31. It is then conveyed on disc 29 within the guide means 31 toward the discharge chute 10. In a manner substantially the same as the operation of disc 3, a sample of the initial sample falls through the holes 30 in disc 29 onto a rotating conveyor disc. This conveyor disc is identical to disc 17 shown in FIG. 3.

This multi-stage sampling procedure can be repeated as many times as desired until a final sample of desired size is produced. The final sample is delivered into the sample chute 34 below the last conveyor disc 17 as shown in FIG. 5. The material passing through the multi-stage sampler is being constantly tumbled and mixed at each stage to produce as representative a sample as possible.

As seen in FIG. 1, a scraper 35 with blade 36 is attached below and rotated by the final conveyor disc 17 to clean the bottom floor of the sampler 1. This prevents material, especially sticky ones, from accumulating on the bottom and contaminating the final sample. A reciprocable scraper 37 is provided above sampler disc 3 to clean its surface between batches. The scraper 37 is moved by piston-cylinder means 38 and arm 39 about shaft 40 as shown in FIG. 2.

As seen in FIGS. 2-5 and 8, inclined chutes 41 are attached to the discharge chute 10 and extend across and below the path of material discharging from each sampler disc. These inclined chutes 41 positively direct this discharge into chute 10 to minimize any tendency of the discharging material to fall on a lower disc. These inclined chutes 41 are particularly useful when light particulate material is being sampled.

I claim:

1. A multi-stage sampler for providing a representative sample of a flowing stream of material, the multi-stage sampler comprising:
   a first conveying means including a movable member with a conveying surface and a drive means for moving said member,
   a first delivery means for delivering material onto said conveying surface,
   a first guide means positioned above the conveying surface in close proximity thereto for guiding the material being conveyed by said first conveying means along a predetermined path across said conveying surface,
   a portion of said conveying surface has at least one hole through it, said driving means moving said portion under said predetermined path so that an initial sample of the material being conveyed by said first conveying means will fall through said hole,
   a second conveying means including a movable member with a conveying surface and a drive means for moving said member,
   a second guide means positioned above the conveying surface of said second conveying means for guiding material being conveyed by said second conveying means along a predetermined path across the conveying surface thereof,
   a portion of said conveying surface of said second conveying means has at least one hole through it, said driving means of said second conveying means moving said portion thereof under the predetermined path defined by said second guide means,
   a second delivery means for delivering material onto the conveying surface of said second conveying means, said second delivery means includes a receiving means positioned below said predetermined path defined by said first guide means to receive said falling initial sample whereby an initial sample of the material delivered onto the conveying surface of the first conveying means passes through the hole therein into the receiving means of the second delivery means which delivers the initial sample onto the conveying surface of the second conveying means which passes a sample of the initial sample through the hole therein.

2. The multi-stage sampler of claim 1 wherein:
   said second delivery means includes a conveying means with a movable member having a conveying surface and a drive means to move said member,
   said receiving means of said second delivery means includes a portion of said conveying surface of the delivery means which is moving underneath said predetermined path across said first conveying surface,
   said second delivery means further includes a guide means for guiding material being conveyed by the conveying means of the second delivery means along a predetermined path across the conveying surface thereof, said guide means including a deflecting means for deflecting material off the conveying surface of the second delivery means onto the conveying surface of the second conveying means.

3. The multi-stage sampler of claim 2 wherein:
   the conveying surfaces of the first and second conveying means and of the second delivery means are each rotated about a substantially vertical axis by their respective drive means, and,
   the first and second guide means and the guide means of the delivery means each includes a stationary support means to hold each guide means stationary relative to its respective rotating, conveying surface.

4. The multi-stage sampler of claim 3 wherein:
   said conveying surfaces are rotated about the same substantially vertical axis.

5. The multi-stage sampler of claim 2 wherein:
   the movable members with the conveying surfaces of said first and second conveying means are rotating discs having a plurality of holes in an annular section near their respective circumferences, and said conveying surface of the second delivery means is a rotating, annular disc off which material is deflected into the hole defined thereby by said deflecting means.

6. The multi-stage sampler of claim 2 including:

a receiver means, a third delivery means for delivering material into said receiver means, said third delivery means includes a movable member with a conveying surface and a drive means for moving said member, said drive means moving a portion of said conveying surface of said third delivery means underneath the predetermined path across said second conveying surface to receive said falling sample whereby the falling sample is received by said third delivery means and delivered to said receiver means.

7. The multi-stage sampler of claim 6 wherein:

said receiver means is an outlet chute, said movable member of said third delivery means has a lower surface with a scraper means depending downwardly therefrom, and a bottom plate below said third delivery means against which the scraper is positioned to clean it.

8. The multi-stage sampler of claim 6 wherein:

said second conveying means and said second guide means define a first sampling apparatus, and said receiver means is a second sampling apparatus identical to said first sampling apparatus whereby said third delivery means receives said falling sample and delivers it onto the conveying surface of said second sampling apparatus which passes a sample thereof.

9. The multi-stage sampler of claim 1 including:

a discharge means, said first and second guide means extend across their respective conveying surfaces to said discharge means whereby the flow across the conveying surfaces of said first and second conveying means that does not pass through their respective holes is discharged into said discharge means, said movable member of said first and second conveying means has a lower surface, and chute means attached to said discharge means and extending below each of said lower surfaces and across the flow discharging from said first and second conveying means to direct the discharge into said discharge means.

* * * * *